US011160510B2

(12) United States Patent
Cadieu et al.

(10) Patent No.: US 11,160,510 B2
(45) Date of Patent: Nov. 2, 2021

(54) VIDEO CLIP SELECTOR FOR MEDICAL IMAGING AND DIAGNOSIS

(71) Applicant: Caption Health, Inc., Brisbane, CA (US)

(72) Inventors: Charles Cadieu, San Francisco, CA (US); Ha Hong, Pleasant Hill, CA (US); Kilian Koepsell, San Francisco, CA (US); Johan Mathe, San Francisco, CA (US); Nicolas Poilvert, Seattle, WA (US); Michael Cannon, Haverford, PA (US); Nathanael Romano, San Francisco, CA (US); Natalia Bilenko, Oakland, CA (US); Charles Chen, San Bruno, CA (US); Nina Miolane, San Francisco, CA (US)

(73) Assignee: Caption Health, Inc., Brisbane, CA (US)

(*) Notice: Subject to any disclaimer, the term of this patent is extended or adjusted under 35 U.S.C. 154(b) by 0 days.

(21) Appl. No.: 17/075,507

(22) Filed: Oct. 20, 2020

(65) Prior Publication Data
US 2021/0106284 A1   Apr. 15, 2021

Related U.S. Application Data

(63) Continuation of application No. 16/839,040, filed on Apr. 2, 2020, now Pat. No. 10,806,402, which is a (Continued)

(51) Int. Cl.
*A61B 5/00*   (2006.01)
*G06N 3/08*   (2006.01)
*G06T 7/00*   (2017.01)

(52) U.S. Cl.
CPC ............ *A61B 5/7221* (2013.01); *A61B 5/004* (2013.01); *A61B 5/0082* (2013.01); *G06N 3/08* (2013.01);
(Continued)

(58) Field of Classification Search
CPC ..... A61B 5/7221; A61B 5/0082; A61B 5/004; G06T 7/0012–0016; G06T 2207/10016;
(Continued)

(56) References Cited

U.S. PATENT DOCUMENTS

| | | | |
|---|---|---|---|
| 2009/0226063 A1* | 9/2009 | Rangwala | ............. G06T 7/0012 382/128 |
| 2015/0269315 A1* | 9/2015 | Arakita | ................ A61B 5/7445 382/131 |

* cited by examiner

*Primary Examiner* — Casey L Kretzer
(74) *Attorney, Agent, or Firm* — Steven M. Greenberg, Esq.; Shutts & Bowen LLP

(57) ABSTRACT

A method for clip selection includes receiving through an interface to a medical imaging device, a selection of a diagnostic procedure and a target portion of a mammalian body. Thereafter, the device acquires video clip imagery of the target portion and stores the video clip imagery in an image store. Each video clip of the video clip imagery is then image processed to determine a view and a quality of each video clip and a rule is retrieved from a rules base corresponding to the selected diagnostic procedure and target portion. In this regard, the rule specifies a requisite view and quality of the video clip imagery. Finally, the retrieved rule is applied to the video clip imagery as a filter to produce a subset of video clip imagery satisfying the specified requisite view and quality and the subset of video clip imagery is stored in the image store.

14 Claims, 2 Drawing Sheets

Related U.S. Application Data continuation of application No. 16/016,725, filed on Jun. 25, 2018, now Pat. No. 10,631,791.

(52) U.S. Cl.
CPC .. *G06T 7/0012* (2013.01); *G06T 2207/10016* (2013.01); *G06T 2207/20081* (2013.01); *G06T 2207/30168* (2013.01)

(58) Field of Classification Search
CPC ........... G06T 2207/30168; G06T 2207/20081; G06N 3/08
See application file for complete search history.

VIDEO CLIP SELECTOR FOR MEDICAL IMAGING AND DIAGNOSIS

CROSS-REFERENCE TO RELATED APPLICATIONS

This application is a Continuation of U.S. patent application Ser. No. 16/839,040, filed Apr. 2, 2020, which is a Continuation of U.S. patent application Ser. No. 16/016,725, filed Jun. 25, 2018, the entirety of each which is incorporated herein by reference.

BACKGROUND OF THE INVENTION

Field of the Invention

The present invention relates to the field of medical imaging and diagnosis and more particularly to video clip selection for use in medical imaging and diagnosis.

Description of the Related Art

Medical imaging refers to the process of creating a visual representation of an interior portion of a mammalian body for the purpose of clinical analysis and medical intervention. Medical imaging seeks to reveal internal structures hidden by the exterior of the body so as to facilitate the diagnosis and treatment of disease. Medical imaging incorporates several different modalities for image acquisition. Common modalities include radiological devices such as X-ray radiography including computerized tomography (CT), magnetic resonance imaging (MRI), medical ultrasonography or ultrasound, endoscopy, elastography, tactile imaging, thermography, medical photography and nuclear medicine functional imaging techniques as positron emission tomography (PET) and Single-photon emission computed tomography (SPECT). Depending upon the desired use of the imagery for the purpose of a medical diagnosis or the targeting of specific tissue or a particular organ or portion of an organ, different modalities for different imagery may be preferred.

Medical imaging of a target area of the body may be achieved from many different views. Strictly speaking, in so far as medical imagery may be two-dimensional in nature, the angle and approach of the imaging device will result in a different perspective view of the target area. As in the case of the modality of medical imaging, a particular view of the target area presented in a medical image may be preferred depending upon the desired use of the imagery for the purpose of a medical diagnosis or the targeting of specific tissue or a particular organ or portion thereof.

Finally, medical imaging of a target area of the body may vary in quality. That is to say, depending upon the operator—usually a technician and not the physician ultimately producing a diagnosis based upon the imagery—the clarity and focal point of a medical image may vary. In some instances, an attempted view of a target organ may be incomplete omitting key features of the target organ from the view due to an improper placement of the imaging sensor. In other instances, external factors such as the anatomical features of the body may inhibit clarity of key features of the target organ despite proper placement of the imaging sensor.

The traditional workflow for medical imaging begins with the use of the imaging modality by a technician upon the patient in order to acquire a set of imagery. The imagery may be still imagery or video clip imagery depending upon the modality. Generally, the technician enjoys an awareness of the ultimate purpose of the imagery so as to diagnose a particular disease or dysfunction of a target organ. Once acquired, the set of imagery is stored in a centralized repository, typically referred to as a "PACS" or "Picture Archival Communications System" and a report, either digital or written, is prepared for review by the physician. The physician then retrieves at a later time the set of imagery and the report and conducts an analysis of the imagery. The analysis generally requires the physician to select the most appropriate images in the set of imagery of the correct views and quality.

This process can be quite tedious—especially given the need for the physician not only to select the correct images of the correct views and quality, but also to efficiently arrange on the display screen the correct images so as to facilitate a diagnosis through the concurrent review of multiple different images of interest. To the extent that the requisite quality of an image does not exist in the set of imagery, but is required, or to the extent that the requisite view of an image does not exist in the set of imagery, the physician must then direct the patient to return for an additional appointment for the technician to re-acquire the missing imagery. So much reflects an enormous waste of resources of the patient, health care facility and physician.

BRIEF SUMMARY OF THE INVENTION

Aspects of embodiments of the invention summarized herein address the foregoing deficiencies and provide a novel and non-obvious method, data processing system and computer program product for clip selection for medical imaging. A method of the invention includes receiving through an interface to a medical imaging device, a selection of a diagnostic procedure and a target portion of a mammalian body. Thereafter, the medical imaging device acquires a multiplicity of video clip imagery of the target portion and stores the video clip imagery in an image store. Each video clip of the video clip imagery is then image processed to determine a view and a quality of each video clip and a rule is retrieved from a rules base corresponding to the selected diagnostic procedure and target portion. In this regard, the rule specifies a requisite view and quality of the video clip imagery so as to achieve a particular measurement necessary in performing the diagnostic procedure. Finally, the retrieved rule is applied to the video clip imagery as a filter to produce a subset of video clip imagery satisfying the specified requisite view and quality and the subset of video clip imagery is stored in the image store.

In one aspect of the embodiment, on the condition that a video clip satisfying the specified requisite view and quality in the video clip imagery is determined upon the application of the retrieved rule not to exist in the video clip imagery, an alert is generated through the interface of the medical imaging device. In another aspect of the embodiment, the image processing of each video clip includes submitting each video clip to a neural network trained to generate output indicating a recognized view in a submitted video clip at a specified level of confidence, or in the alternative, submitting each video clip to a content based image retrieval system adapted to compare a submitted video clip to a data store of known images of particular views so as to indicate a recognized view in the submitted video clip.

In yet another aspect of the embodiment, the image processing of each video clip further includes computationally computing a generalized degree of quality of a submitted image based upon the specified level of confidence produced in the output of the neural network. Finally, in even yet another aspect of the embodiment, the rule additionally specifies a requisite presence of a landmark feature in the view. In this way, the image processing of each video clip includes submitting each video clip to a neural network trained to generate output indicating a recognized landmark feature in a submitted video clip at a specified level of confidence, such that during application of the retrieved rule, an absence of the landmark feature correlates to poor quality of the video clip, but a presence of the landmark feature correlates to good quality of the video clip.

In another embodiment of the invention, a medical imaging data processing system is configured for clip selection. The system includes a host computing system that includes one or more computers, each with memory and at least one processor. A diagnostic imaging computer program executes in the memory of the host computing system and provides control instructions to a communicatively coupled medical imaging device. The program additionally provides an interface to the medical imaging device.

Importantly, the program yet further includes computer program instructions enabled during execution to perform a method of clip selection for medical imaging. The method includes receiving through an interface to a medical imaging device, a selection of a diagnostic procedure and a target portion of a mammalian body. Thereafter, the medical imaging device acquires a multiplicity of video clip imagery of the target portion and stores the video clip imagery in an image store. Each video clip of the video clip imagery is then image processed to determine a view and a quality of each video clip and a rule is retrieved from a rules base corresponding to the selected diagnostic procedure and target portion. In this regard, the rule specifies a requisite view and quality of the video clip imagery. Finally, the retrieved rule is applied to the video clip imagery as a filter to produce a subset of video clip imagery satisfying the specified requisite view and quality and the subset of video clip imagery is stored in the image store.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Embodiments of the invention provide for video clip selection for medical device imaging and diagnostics. In accordance with an embodiment of the invention, a set of contemporaneously acquired video clips of a mammalian organ are selected for processing and each video clip in the set is submitted to a neural network trained to classify each video clip according to a particular view of the organ and a modality utilized to acquire the video clip. The confidence produced by the neural network serves as input to a function determinate of a quality of the video clip. An intended use of the acquired video clips is then specified, for example, to compute a measurement of the organ in furtherance of the computation of a measurement in respect to a specified diagnostic procedure, and a rule from a rules base retrieved indicating a specific view, modality and quality requirement for the intended use. Optionally, the rule indicates a presentation arrangement of video clips in a viewer. Based upon the indication by the rule of the specific view, modality and quality requirement for the intended use, the acquired video clips are filtered to produce a subset of video clips of the specific view, modality and quality. Finally, the subset of video clips is provided as input to a diagnostic viewer presenting the subset of video clips for viewing by a health care professional. Optionally, the viewer arranges the presentation of the subset of video clips in accordance with the rule. In particular, the arrangement of the presentation of the subset of the video clips may include a re-ordering of the subset of the video clips so that the most relevant ones of the video clips are first presented to the health care professional.

Figure 1:
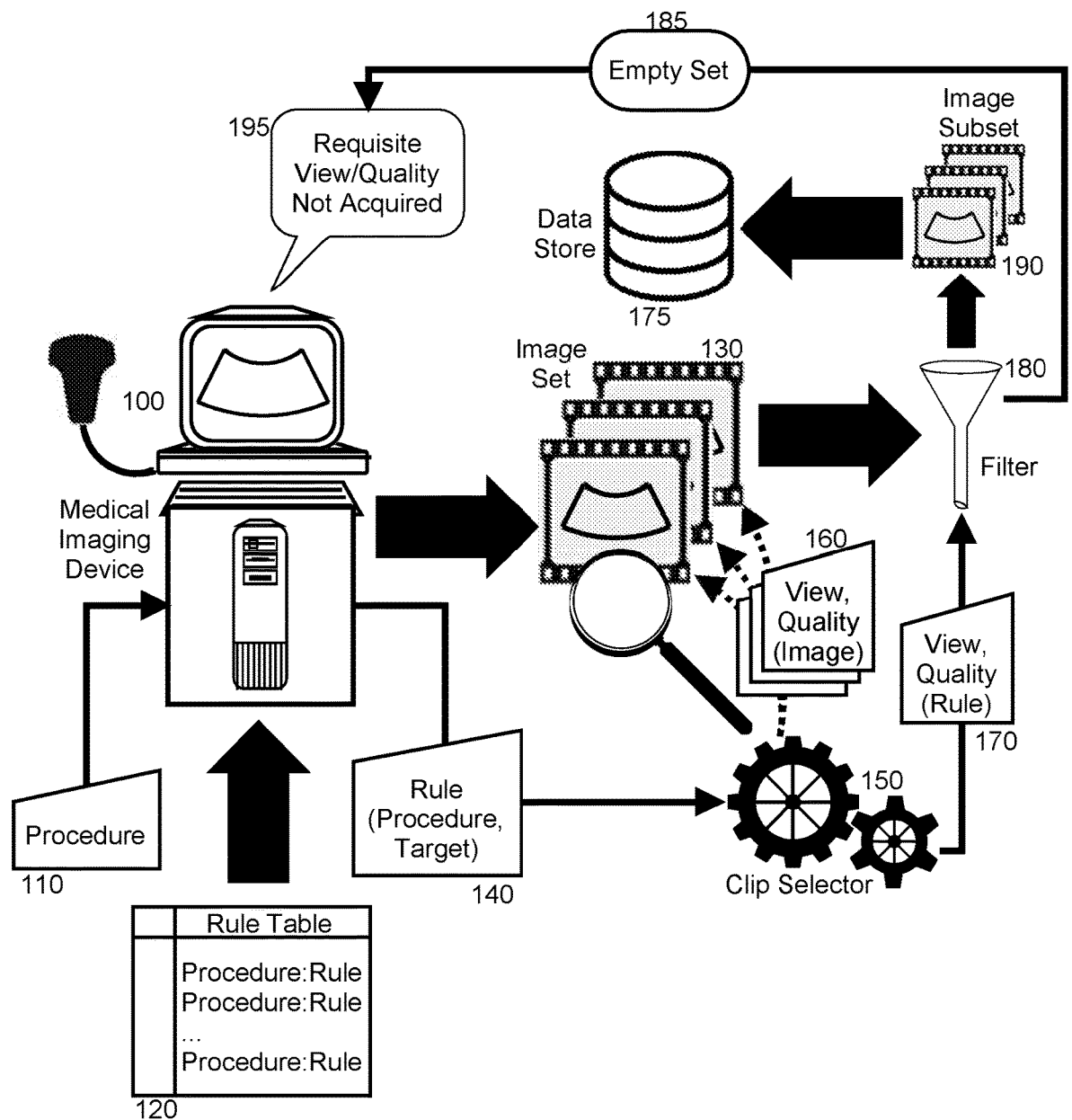
FIG. 1 is a pictorial illustration of a process for clip selection for medical imaging.

In further illustration, FIG. 1 is a pictorial illustration of a process for clip selection for medical imaging. As shown in FIG. 1, a medical imaging device 100 acquires imagery in an image set 130 of a target organ in a mammalian body. Each image in the image set 130 reflects a specific view of the target organ and has a particular quality. Chip selector logic 150 loads each of the images in the image set 130 and determines both a view reflected by the image and also a determined quality 160. Thereafter, an intended procedure 110 is specified to the medical imaging device 100 and a specific rule 140 as to the requisite quality and view of imagery is selected from a rule table 120 based upon the intended procedure 110 and optionally, a specified measurement to be computed in furtherance of the intended procedure 110. The selected rule 140 is provided to the chip selector logic logic 150.

The chip selector logic 150 applies the selected rule 140 to each image in the image set 130 so as to create a filter 180 filtering or sorting (re-ordering) the image set 130 into an image subset 190 of only those images having an assigned view and quality 160 sufficient to support the specified procedure 110 and optionally, in an order with the most desirable view and quality positioned at a top of the ordering. Thereafter, to the extent that the chip selector logic 150 determines that one or more images are present in the image subset 190, the image subset 190 is stored in data store 175 for use in a medical diagnosis of the specified procedure 110. Otherwise, the chip selector logic 150 upon detecting an empty set 185 for the image subset 190 directs a prompt 195 in the medical imaging device 100 indicating a need to re-acquire new imagery satisfying of either or both of requisite view or a requisite quality for the specified procedure 110.

Figure 2:
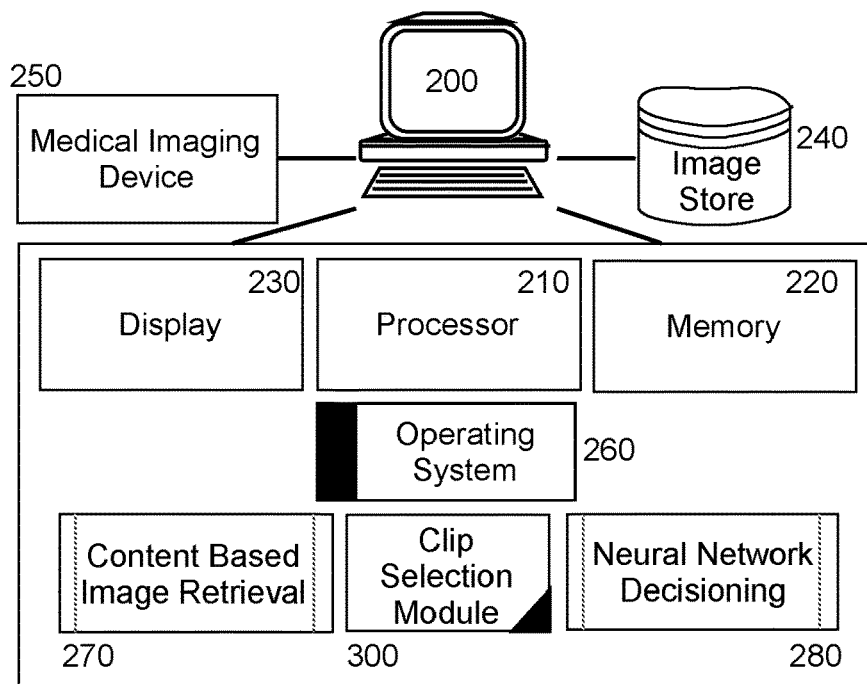
FIG. 2 is a schematic illustration of a data processing system configured for clip selection for medical imaging; and, FIG. 3 is a flow chart illustrating a process for clip selection for medical imaging.

The process described in connection with FIG. 1 may be implemented in a data processing system. In further illustration, FIG. 2 schematically shows a data processing system configured for clip selection for medical imaging. The system includes a host computing system 200 that includes memory 220, at least one processor 210 and a display 230. The host computing system 200 also is coupled to a medical imaging device 250 adapted to acquire medical imagery of target organs, and an image store 240 into which the acquired medical imagery is stored. An operating system 260 executes in the memory 220 of the host computing system 200. The operating system 260 supports the execution of program code of a clip selection module 300.

The program code of the clip selection module 300 is enabled upon execution by the processor 210 in the memory 220 to receive in an interface to the medical imaging device 250, an indication of a procedure in respect to a target organ, along with a set of images in image store 240 acquired by the medical imaging device 250 in respect to the indicated procedure. The program code further is enabled during execution to analyze and assign to each image in the image set both a view and a quality of each image. In this regard, the program code of the clip selection module 300 may provide each image in the image set to a neural network 280 trained to produce a probabilistic indication of a quality and view for a provided image. Alternatively, the program code of the clip selection module 300 may provide each image to a content based image retrieval system 270 able to compare the imagery of each image to a known set of imagery in order to classify each image in respect to a particular view and a particular quality based upon imagery of a known view and a known quality.

Optionally, the content based image retrieval system 270 may indicate a quality based upon an appearance in an image of a landmark portion of the mammalian body expected to be shown in respect to the particular view of the image. Absence of the landmark indicates poor quality. Vary degrees of presence of the landmark indicates vary degrees of quality. For instance, a clear presence of a landmark in an image when expected indicates good quality. Conversely, partial presence of the landmark indicates mediocre quality.

As another option, an echo distance can be computed to each image in terms of a disparity between a pose of an image acquisition device resulting in the image, and an optimum pose. More specifically, a set of training images each annotated with a known pose utilized to acquire a corresponding one of the training images, and optionally a deviation from an a priori known optimal pose to acquire a highest quality form of the training image, are correlated so that a subsequent image, when compared to the training images, can result in identification of a likely pose variation referred to as an echo distance. The foregoing may be achieved through content-based image retrieval or through a neural network trained with the training images to indicate the echo distance. A quality is then assigned to the subsequent image based upon a correlated echo distance such that a threshold echo distance indicates poorer quality than a smaller echo distance for the subsequent image.

As another option, the neural network 280 may indicate a recognized view in a submitted video clip at a specified level of confidence.

Once the program code of the clip selection module 300 has established a computed view and quality for each image in the image set, the program code is further enabled to select a particular rule from a rules-base keyed upon the indicated procedure and to apply the rule to each image in the image set. In this regard, the determined view and quality of each image in the image set is provided as input to the particular rule in order to determine of the view and quality exceeds that required by the particular rule. If so, the image is added to a subset of images in the image store 240. Otherwise, the image is discarded. Once each image in the image set has been processed by the particular rule, the program code of the clip selection module 300 determines if any images persist in the subset in the image store 240. If not, the clip selection module 300 directs the medical imaging device 250 to generate an alert in the interface indicating a necessity to acquire additional imagery.

Figure 3:
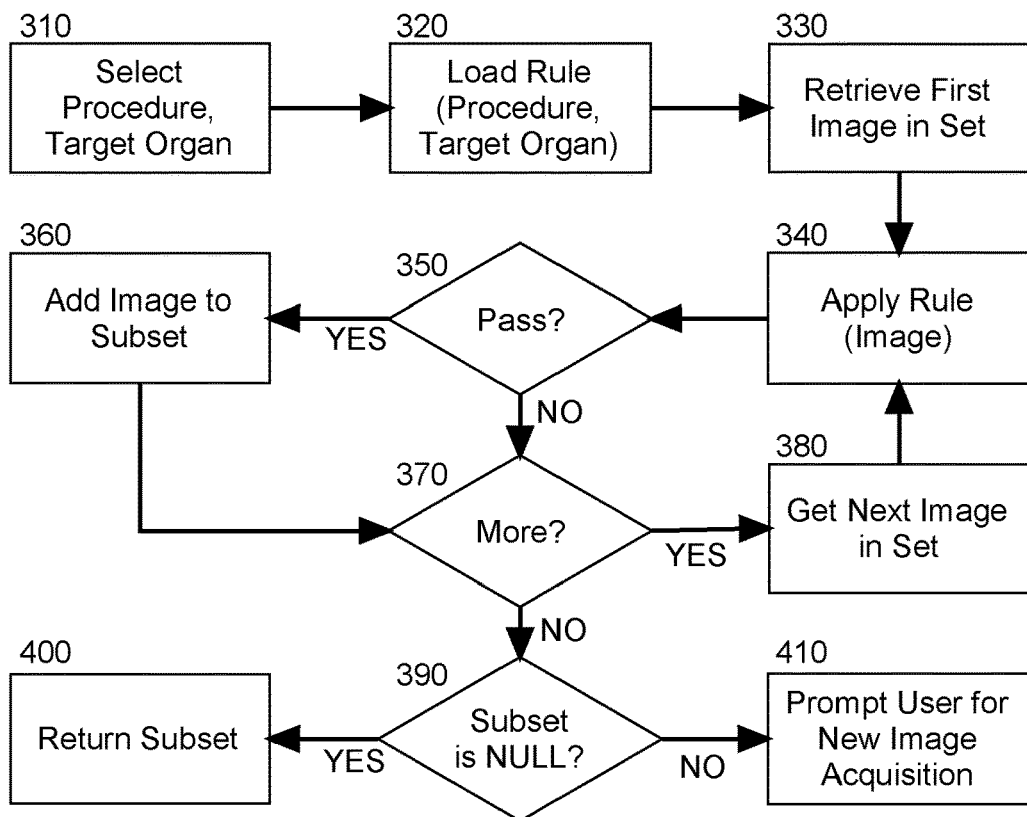

In even yet further illustration of the operation of the clip selection module 300, FIG. 3 is a flow chart illustrating a process for clip selection for medical imaging. The processing begins in block 310 in which a target procedure and target organ is specified in an interface to the medical imaging device. In block 320, a rule is located for the specified target procedure and target organ. Thereafter, in block 330, a first image in an image set is retrieved from the data store and an assigned quality and view loaded into memory. Optionally, the retrieval occurs in real-time during the acquisition of the image set by the medical imaging device. In block 340, the located rule is applied to the assigned quality and view in order to determine in decision block 350. In decision block 350, if the first image is of sufficient quality and view for the specified target procedure and target organ, the first image is added to a subset in block 360. Otherwise, the process continues in decision block 370.

In decision block 370, if additional images remain to be processed, in block 380, a next image in the image set is selected for processing and the process repeats through block 340 with the application of the located rule. Otherwise, in decision block 390 it is then determined if any images exist in the subset. If so, in block 400 the subset is returned for utilization in a diagnostic analysis of the target procedure. But otherwise, in block 410 a prompt in an interface to the medical imaging device is presented indicating a need to acquire additional imagery of the requisite quality, the requisite view, or both.

The present invention may be embodied within a system, a method, a computer program product or any combination thereof. The computer program product may include a computer readable storage medium or media having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Computer readable program instructions described herein can be downloaded to respective computing/processing devices from a computer readable storage medium or to an external computer or external storage device via a network. The computer readable program instructions may execute entirely on the user's computer, partly on the user's computer, as a stand-alone software package, partly on the user's computer and partly on a remote computer or entirely on the remote computer or server. Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Finally, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows.

We claim:

1. A method for clip selection for medical imaging comprising:
   receiving through an interface to a medical imaging device, a selection of a diagnostic procedure and a target portion of a mammalian body;
   acquiring a multiplicity of video clip imagery of the target portion utilizing the medical imaging device;
   storing the video clip imagery in an image store;
   image processing each video clip of the video clip imagery to determine different measurements of the target portion;
   retrieving a rule from a rules base corresponding to the selected diagnostic procedure and target portion, the rule specifying a requisite one of the measurements of the target portion;
   applying the retrieved rule to the video clip imagery as a filter to produce a subset of video clip imagery satisfying the specified requisite one of the measurements of the target portion; and,
   storing the subset of video clip imagery in the image store.

2. The method of claim 1, further comprising:
   on condition that a video clip satisfying the specified requisite one of the measurements of the target portion in the video clip imagery is determined upon the application of the retrieved rule not to exist in the video clip imagery, generating an alert through the interface of the medical imaging device.

3. The method of claim 1, wherein the image processing of each video clip comprises submitting each video clip to a neural network trained to generate output indicating a recognized measurement in a submitted video clip at a specified level of confidence.

4. The method of claim 1, wherein the image processing of each video clip comprises submitting each video clip to a content-based image retrieval system adapted to compare a submitted video clip to a data store of known images of particular measurements so as to indicate a recognized measurement in the submitted video clip.

5. The method of claim 1, wherein the storing occurs during real-time acquisition of the multiplicity of video clip imagery of the target portion utilizing the medical imaging device.

6. A medical imaging data processing system configured for clip selection, the system comprising:
   a host computing system comprising one or more computers, each including memory and at least one processor;
   a diagnostic imaging computer program executing in the memory of the host computing system, the program providing control instructions to a communicatively coupled medical imaging device, the program additionally providing an interface to the medical imaging device, the program yet further comprising computer program instructions enabled during execution to perform:
   receiving through the interface a selection of a diagnostic procedure and a target portion of a mammalian body;
   acquiring a multiplicity of video clip imagery of the target portion utilizing the medical imaging device;

storing the video clip imagery in an image store;
image processing each video clip of the video clip imagery to determine different measurements of the target portion;
retrieving a rule from a rules base corresponding to the selected diagnostic procedure and target portion, the rule specifying a requisite one of the measurements of the target portion;
applying the retrieved rule to the video clip imagery as a filter to produce a subset of video clip imagery satisfying the specified requisite one of the measurements of the target portion; and,
storing the subset of video clip imagery in the image store of the host computing system.

7. The system of claim 6, wherein the program instructions are further enabled to perform:
on condition that a video clip satisfying the specified requisite one of the measurements of the target portion in the video clip imagery is determined upon the application of the retrieved rule not to exist in the video clip imagery, generating an alert through the interface of the medical imaging device.

8. The system of claim 6, wherein the image processing of each video clip comprises submitting each video clip to a neural network trained to generate output indicating a recognized measurement in a submitted video clip at a specified level of confidence.

9. The system of claim 6, wherein the image processing of each video clip comprises submitting each video clip to a content-based image retrieval system adapted to compare a submitted video clip to a data store of known images of particular measurements so as to indicate a recognized measurement in the submitted video clip.

10. A computer program product for clip selection for medical imaging, the computer program product including a non-transitory computer readable storage medium having program instructions embodied therewith, the program instructions executable by a device to cause the device to perform a method including:
receiving through an interface to a medical imaging device, a selection of a diagnostic procedure and a target portion of a mammalian body;
acquiring a multiplicity of video clip imagery of the target portion utilizing the medical imaging device;
storing the video clip imagery in an image store;
image processing each video clip of the video clip imagery to determine different measurements of the target portion;
retrieving a rule from a rules base corresponding to the selected diagnostic procedure and target portion, the rule specifying a requisite one of the measurements of the target portion;
applying the retrieved rule to the video clip imagery as a filter to produce a subset of video clip imagery satisfying the specified requisite one of the measurements of the target portion; and,
storing the subset of video clip imagery in the image store.

11. The computer program product of claim 10, wherein the method performed by the device further comprises:
on condition that a video clip satisfying the specified requisite one of the measurements of the target portion in the video clip imagery is determined upon the application of the retrieved rule not to exist in the video clip imagery, generating an alert through the interface of the medical imaging device.

12. The computer program product of claim 10, wherein the image processing of each video clip comprises submitting each video clip to a neural network trained to generate output indicating a recognized measurement in a submitted video clip at a specified level of confidence.

13. The computer program product of claim 10, wherein the image processing of each video clip comprises submitting each video clip to a content based image retrieval system adapted to compare a submitted video clip to a data store of known images of particular measurements so as to indicate a recognized measurement in the submitted video clip.

14. The computer program product of claim 10, wherein the storing occurs during real-time acquisition of the multiplicity of video clip imagery of the target portion utilizing the medical imaging device.

\* \* \* \* \*